(12) United States Patent
Tancredi et al.

(10) Patent No.: US 8,290,119 B2
(45) Date of Patent: Oct. 16, 2012

(54) ADJUSTABLE SCANNER

(75) Inventors: Henry Tancredi, Ottsville, PA (US); Edward Marandola, Gwynedd, PA (US); John Tancredi, Hatfield, PA (US)

(73) Assignee: Imaging Sciences International LLC, Hatfield, PA (US)

( * ) Notice: Subject to any disclaimer, the term of this patent is extended or adjusted under 35 U.S.C. 154(b) by 201 days.

(21) Appl. No.: 12/524,403

(22) PCT Filed: Jan. 24, 2008

(86) PCT No.: PCT/US2008/051922
§ 371 (c)(1),
(2), (4) Date: Mar. 1, 2010

(87) PCT Pub. No.: WO2008/092009
PCT Pub. Date: Jul. 31, 2008

(65) Prior Publication Data
US 2010/0172462 A1    Jul. 8, 2010

Related U.S. Application Data

(60) Provisional application No. 60/897,421, filed on Jan. 24, 2007.

(51) Int. Cl.
*A61B 6/14* (2006.01)
(52) U.S. Cl. .......................................... 378/38; 378/197
(58) Field of Classification Search .................... 378/38, 378/39, 4, 197, 198, 37
See application file for complete search history.

(56) References Cited

U.S. PATENT DOCUMENTS

| | | | |
|---|---|---|---|
| 5,131,844 A | 7/1992 | Marinaccio et al. |
| 5,355,398 A | 10/1994 | Nakano et al. |
| 5,448,610 A | 9/1995 | Yamamoto et al. |
| 5,600,699 A | 2/1997 | Suzuki et al. |
| 5,666,392 A | 9/1997 | Ploetz |

(Continued)

FOREIGN PATENT DOCUMENTS
EP    1721574    11/2006

OTHER PUBLICATIONS

PCT/US2009/034750 International Search Report and Written Opinion, 11 pages, dated Apr. 3, 2009.

(Continued)

*Primary Examiner* — Hoon Song
(74) *Attorney, Agent, or Firm* — Michael Best & Friedrich LLP

(57) ABSTRACT

For dental and facial imaging, a source of x-rays (14) or other penetrating radiation and a detector (20) are mounted opposite one another on a rotatable gantry (28), so that the head of the patient can be positioned between the source (14) and the detector (20), with the axis of rotation (36) of the gantry passing through the patient's head. The detector is longer in one direction than in the perpendicular direction, generally rectangular, and is rotatable between a position in which the long axis is transverse to the axis of rotation of the gantry and a position in which the long axis is generally parallel to the axis of rotation of the gantry. The length of the detector along the long axis is sufficient for fully detailed computed CT when the long axis is transverse, and for full-face CT when the long axis is parallel.

24 Claims, 7 Drawing Sheets

U.S. PATENT DOCUMENTS

| | | | |
|---|---|---|---|
| 5,997,176 | A | 12/1999 | Fairleigh |
| 6,055,292 | A | 4/2000 | Zeller et al. |
| 6,118,842 | A | 9/2000 | Arai et al. |
| 6,412,978 | B1* | 7/2002 | Watanabe et al. ............. 378/197 |
| 8,005,186 | B2* | 8/2011 | Lee ................................. 378/38 |
| 2001/0036246 | A1* | 11/2001 | Graumann ................... 378/197 |
| 2002/0085681 | A1* | 7/2002 | Jensen ......................... 378/197 |
| 2004/0190678 | A1 | 9/2004 | Rotondo et al. |
| 2004/0264624 | A1 | 12/2004 | Tanaka et al. |
| 2005/0254620 | A1* | 11/2005 | Shoji et al. ...................... 378/37 |
| 2006/0067464 | A1 | 3/2006 | Clinthorne et al. |
| 2006/0116566 | A1 | 6/2006 | Bruijns |
| 2006/0239400 | A1 | 10/2006 | Sukovic et al. |

OTHER PUBLICATIONS

PCT/US2008/051922 International Search Report.
EP 09713389.6 Extended European Search Report and Opinion dated Dec. 23, 2010 (9 pages).
Office Action from the State Intellectual Property Office of the People's Republic of China for Application No. 200980105314.5 dated May 2, 2012 (English Translation and Original, 12 pages).

* cited by examiner

ADJUSTABLE SCANNER

STATEMENT OF PRIORITY

This application claims priority to U.S. provisional application 60/897,421 filed Jan. 24, 2007, and incorporated by reference herein.

TECHNICAL FIELD

The invention relates to the examination of objects with penetrating radiation, and especially to a scanner with a detector that can be positioned in different orientations to generate different images.

BACKGROUND

The viewing of objects, including parts of the human anatomy, by the use of x-rays and other forms of penetrating radiation is known. In the case of x-rays, the radiation is directed at the object from one side, and the part of the radiation that penetrates the object is detected at the opposite side. An image may thus be obtained in which parts of the object that are more absorbent of x-rays, typically more dense parts of the object, appear as darker shadows, for example, by detecting the x-rays electronically and generating an image using a computer. In a computed tomography (CT) system, a series of x-ray images of a target are taken with the direction from the source to the detector differently oriented relative to the target. From these images, a three-dimensional representation of the density of x-ray absorbing material in the target may be reconstructed. Other methods of generating a three-dimensional dataset are known, or may be developed hereafter. From the three-dimensional data, a tomogram, which is a section in a desired plane, may be generated.

In a typical dental CT system, the patient sits upright, and the x-ray source and detector are mounted on opposite ends of a gantry that rotates about a vertical axis through the middle of the patient's head. In order to obtain sufficient data to cover the desired part of the head, which is most of the extent of the skull in the horizontal plane in CT imaging with high resolution, the detector must span a substantial distance in the circumferential direction perpendicular to the axis of rotation of the gantry, that is to say, the horizontal, direction.

Electronic detectors currently available include flat panel arrays of charge-coupled device (CCD) or other detectors, each of which converts incoming x-rays over a defined pixel area in a defined time to an electric charge that can easily be converted to a digital intensity value for subsequent computation. One flat panel detector commercially available from Varian Medical Systems, Inc., of Salt Lake City, Utah that is suitable for use in dental CT units has a pixel size of 127 μm (micrometers) square, and has an overall panel size of approximately 25 cm×20 cm. In dental imaging with a cone beam, because of the divergence of the beam towards the panel, that panel provides an effective Field of View approximately 16 cm×13 cm. When mounted with the long axis horizontal, the 25 cm length of the panel thus allows a Field of View with a diameter of approximately 16 cm, which is large enough to permit sufficient coverage of the imaged structures in the axial (horizontal) direction with high resolution for typical dental uses.

However, for most normal adults, the 20 cm height of the panel allows imaging only from the bottom of the lower jaw to about the bottoms of the orbits of the eyes (about 13 cm effective height at the level of the object being viewed). That is sufficient for most dental and oral surgery applications, but for some classes of orthodontic and orthognathic surgery applications an x-ray image up to the level of the glabella, roughly the level of the eyebrows, is essential. Such images, known as "full face" have in the past been produced by conducting two overlapping scans of 13 cm height at different levels and merging the images. Conducting two scans increases the radiation dose to the patient. Merging the images seamlessly is difficult, especially as the time taken to reposition the gantry, or the patient, between the two scans allows the patient to move. It would be possible to use a 25 cm square detector panel, which would have both the width to produce full coverage CT scans of the mouth diametrally, and the height to produce full-face scans in a single scan for about 98% of human adults, but the cost of detector panels increases disproportionately to the size of the panel, and could not easily be justified, when the full height is seldom required.

SUMMARY

According to one embodiment of the invention, there is provided a method and system for dental and facial computed tomography or other imaging, in which a source of x-rays or other penetrating radiation and a flat-panel detector for the radiation are mounted opposite one another on a rotatable gantry, so that the head of the patient can be positioned between the source and the detector, with the axis of rotation of the gantry passing through the patient's head. The detector is longer in one direction than in the perpendicular direction, generally rectangular, and is rotatable between a position in which the long axis of the detector is generally perpendicular to and a position in which the long axis is generally parallel to the axis of rotation of the gantry. The length of the detector panel along the long axis is sufficient for fully detailed computed CT when the long axis is perpendicular to the axis of rotation of the gantry, and for full-face CT when the long axis is parallel to the axis of rotation of the gantry.

The "vertical" direction is defined relative to the orientation of the patient's head when the patient is standing or sitting upright. Although for ease of construction and operation this direction and the direction of the axis of rotation of the gantry are substantially aligned and substantially the same as local gravitational vertical, consideration of the geometry and mechanics of the system, and the motility and flexibility of human beings, shows that exact alignment is not necessary. In addition, some dental x-ray machines operate with the patient lying down, and the "vertical" direction of the patient's head is then more nearly horizontal relative to gravity.

In one disclosed embodiment, the detector panel is aligned so that with the long axis perpendicular to the gantry rotation axis (landscape orientation) the center of the panel is on the center axis of the beam of radiation from the source, which center axis intersects the axis of rotation of the gantry.

In a disclosed embodiment the detector panel is mounted so that one bottom corner is in the same position in both the landscape orientation and the orientation with the long axis parallel to the gantry rotation axis (portrait orientation). Using this feature, or in other embodiments, in the portrait orientation the panel may extend more above the center of the beam, and less to the other side of the beam, than in the landscape orientation. Where the landscape orientation is optimized for imaging the mouth, the portrait orientation can then be optimized for full-face imaging at the same relative position of the patient's head and the scanner gantry. Where the landscape orientation is optimized for high resolution, the portrait orientation, extending as far from the axis as the landscape orientation on one side but less far on the other side, can provide a good compromise to maintain acceptable resolution with the narrower panel.

The invention also provides computer software arranged to generate 3-D tomographic and other datasets and tomographic and other images in accordance with the method of the invention, and computer-readable media containing such software. The software may be written to run on an otherwise conventional computer processing tomographic data.

The computer software may be responsive to a signal from a switch that detects the position of the sensor panel.

The invention also provides data produced by the methods and systems of the invention.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Reference will now be made in detail to various embodiments of the present invention, examples of which are illustrated in the accompanying drawings.

Figure 1:
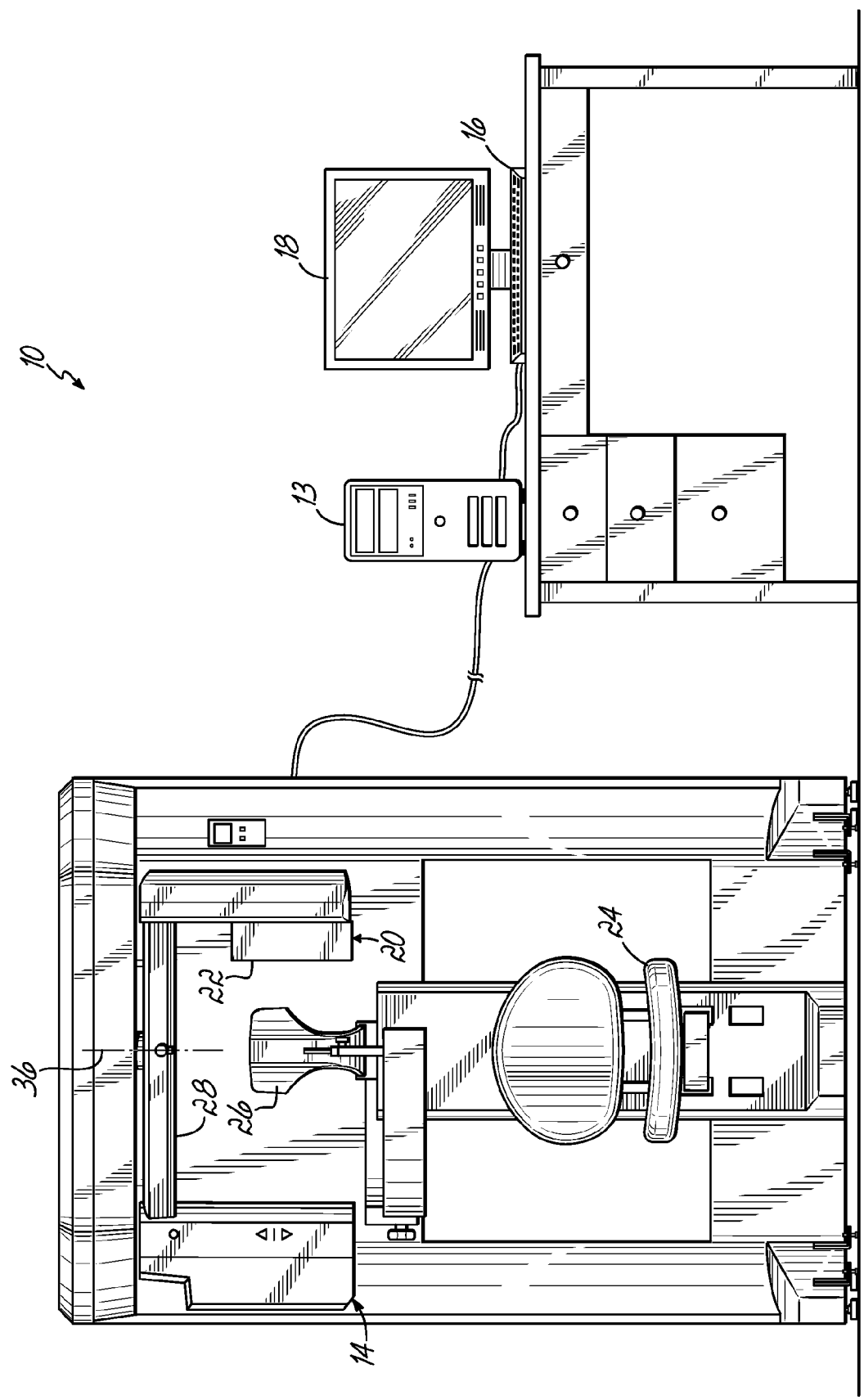
FIG. 1 is a schematic view of apparatus for generating a tomographic image.
Figure 2:
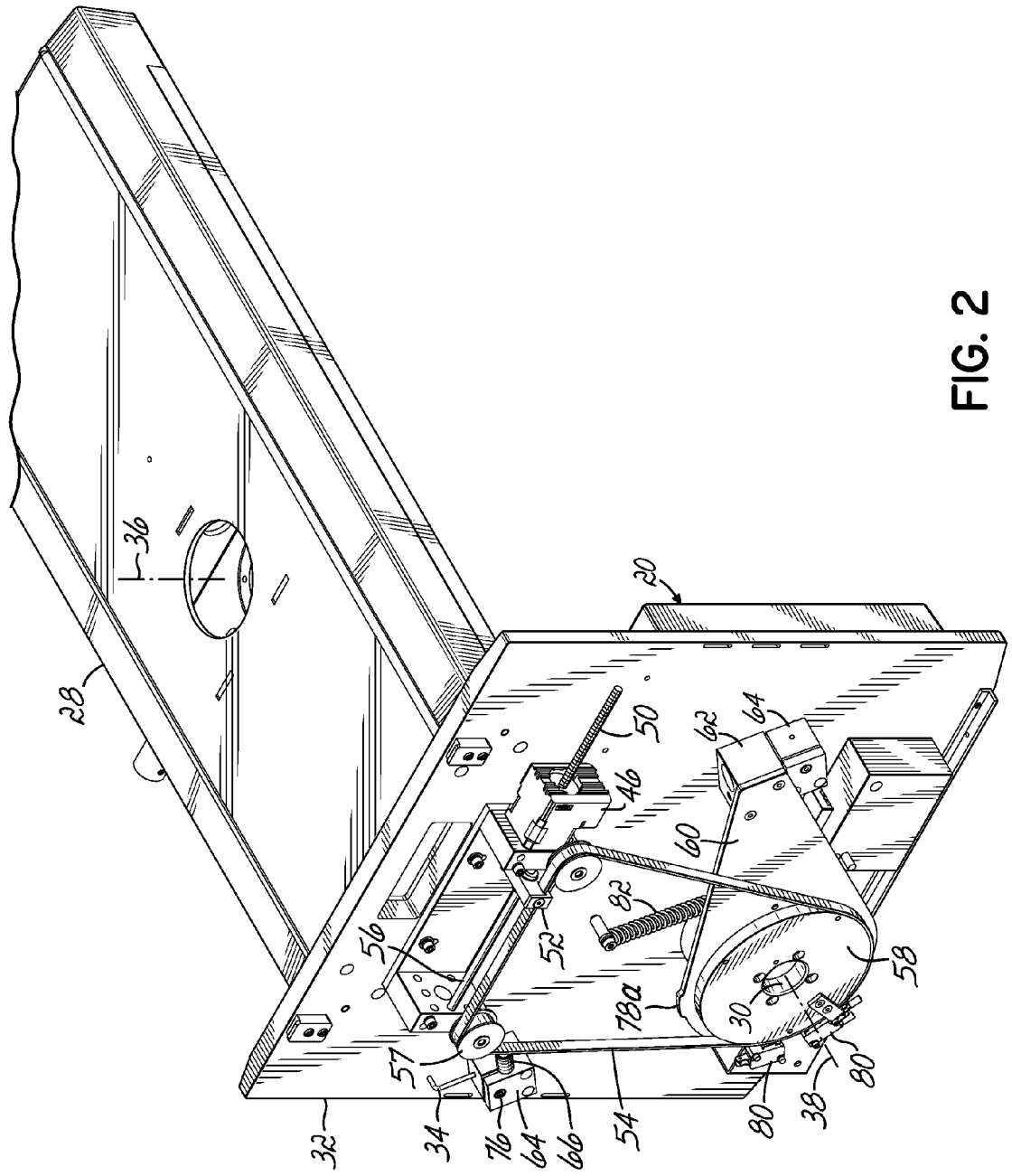
FIG. 2 is a perspective view of part of a gantry of the apparatus of FIG. 1, with a cover removed.

Referring to the drawings, and initially to FIGS. 1 and 2, one form of tomographic apparatus 10 according to an embodiment of the invention, comprises a scanner 12 and a computer 13 controlled by a console 16 with a display 18. The scanner 12 comprises a source of x-rays 14, an x-ray detector 20 including a rectangular sensor array 22, and a support 24 for an object to be imaged. In an embodiment, the scanner 12 is arranged to image the head, or part of the head, of a human patient (not shown), especially the jaws and teeth. The support 24 may then be a seat with a rest or restrainer 26 for the head or face (not shown) of the patient. The x-ray source 14 and x-ray detector 20 are then mounted on a rotating carrier or gantry 28 so as to circle round the position of the patient's head, while remaining aligned with one another. The x-ray detector 20 then records a stream of x-ray shadowgrams of the patient's head from different angles. The computer 13 receives the x-ray image data from the scanner 12, and calculates a 3-dimensional spatial distribution of x-ray density.

The imaging of the patient's head and calculation of the spatial distribution may be carried out by methods and apparatus already known in the art and, in the interests of conciseness, are not further described here. Suitable apparatus is available commercially, for example, the i-CAT Cone Beam 3-D Dental Imaging System from Imaging Sciences International of Hatfield, Pa.

Figure 3:
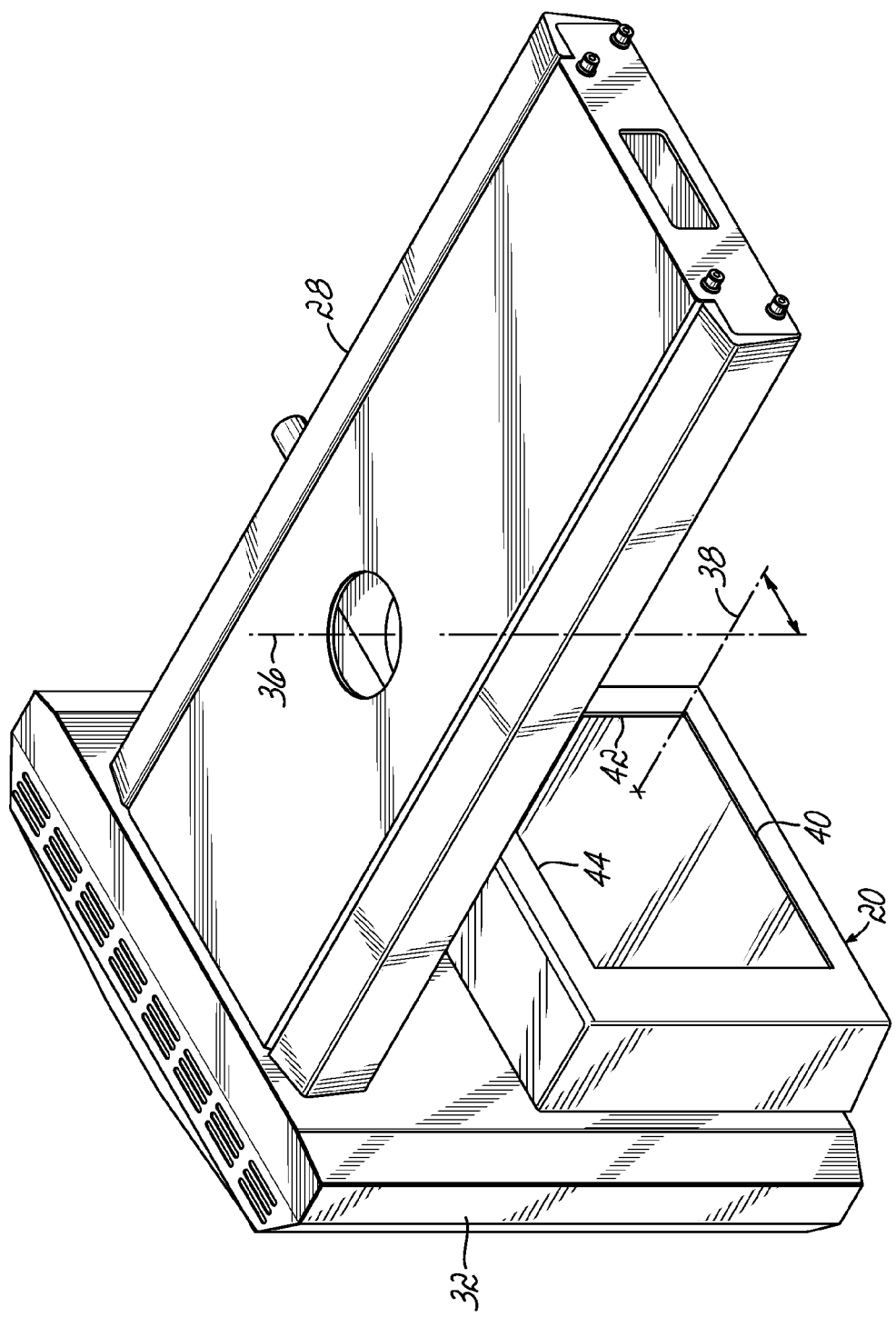
FIG. 3 is a different perspective view of the same part of a gantry as in FIG. 2.

Referring now also to FIG. 2 and FIG. 3, the x-ray detector 20 comprises a panel having a rectangular array of x-ray sensitive elements, supported by a cylindrical roller bearing 30 on a mounting panel 32 attached to the gantry 28. Not shown are electrical cables and a guard that protects the cables from the moving parts. The electrical cables are partially retained between a guide 34 and the mounting panel 32. The x-ray source 14 is arranged to emit a beam of x-rays with an axis (the x-ray axis, not shown) that is aligned with the center of the x-ray source 14, and intersects perpendicularly the gantry axis of rotation 36 of the gantry 28 relative to the frame of the scanner 12. The axis 38 of the roller bearing 30 ("the detector axis") may be parallel to but offset from the x-ray axis of source 14. The panel of the x-ray detector 20 is generally perpendicular to the detector axis 38, and the detector axis passes through the panel. In the embodiments shown, when the x-ray detector 20 is in the landscape orientation with the long axis of the rectangular sensor array 22 horizontal (perpendicular to the gantry axis 36), the x-ray axis is aligned with the center of the rectangular sensor array 22.

Figure 5A:
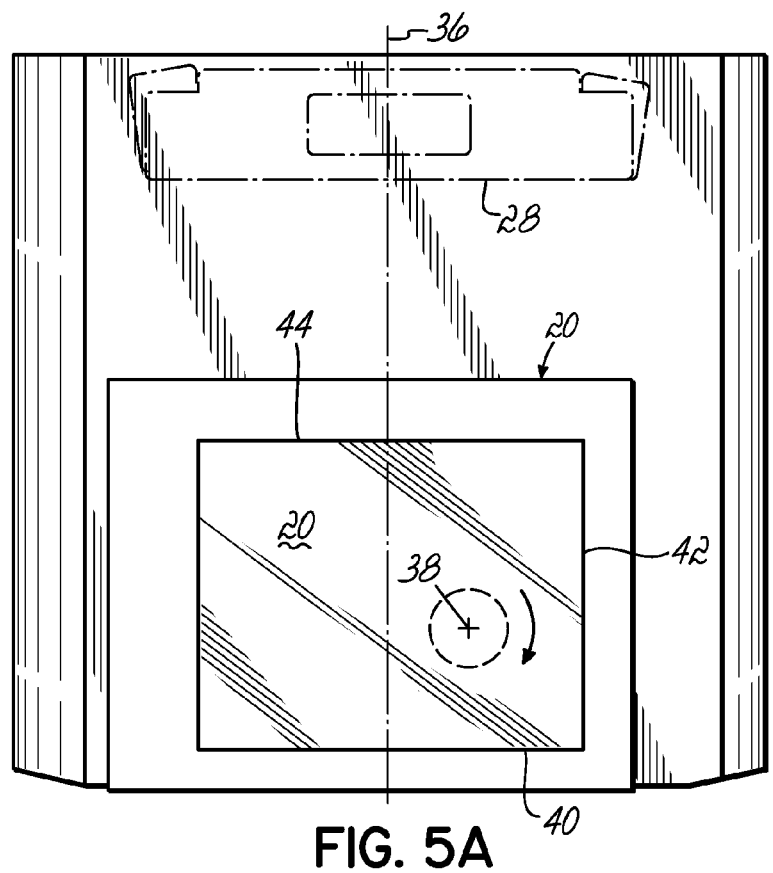
FIG. 5A is an elevational view of the interior side of the detector end in landscape orientation.
Figure 5B:
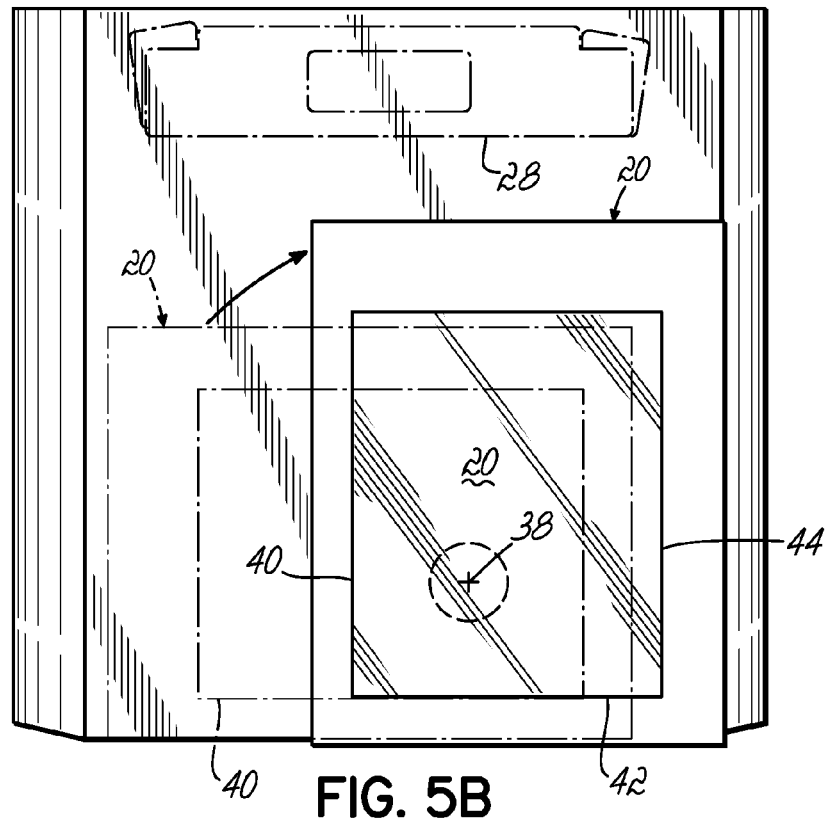
FIG. 5B is an elevational view of the interior side of the detector end in portrait orientation

The detector axis 38 is offset horizontally from the x-ray axis, and is positioned equal distances from the bottom, and one end of the rectangular sensor array 22. For an example using numbers, in one embodiment, the panel has a rectangular sensor array 22 with an operative area 20 cm by 25 cm, and the detector axis 38 is then 10 cm from each of the bottom edge 40 and one end 42 (the left end as seen in FIG. 2 or the right end as seen in FIGS. 3, 5A, and 5B) of the array. Then, when the x-ray detector 20 is rotated 90° about the detector axis 38 from the landscape orientation seen in FIG. 5A to a portrait orientation FIG. 5B, the detector assumes a position where the bottom short edge 42 in portrait orientation is on the same line as the bottom long edge 40 in landscape orientation.

An additional embodiment also contemplated, but not shown, is as follows: The detector axis 38 is offset horizontally from the x-ray axis, and is positioned equal distances from the top edge 44, bottom edge 40, and one end 42 of the rectangular sensor array 22. For an example, using the same numbers as in the embodiment shown, the panel has a rectangular sensor array 22 with an operative area 20 cm by 25 cm, and the detector axis 38 is then 10 cm from each of the top, bottom, and one end (the left end as seen in FIG. 2) of the array. Then, when the x-ray detector 20 is rotated 90° about the detector axis 38 from the landscape orientation a portrait orientation, the detector assumes a position (not shown) where the left-hand long edge in portrait orientation is on the same line as the left-hand short edge in landscape orientation, and the bottom long edge in portrait orientation is on the same line as the left-hand short edge in landscape orientation.

The roller bearing 30 is a large-diameter bearing, for example, 5.5 cm diameter, with minimal play and backlash. A high-resolution imaging panel 20 may have a pixel size of for example, 127 µm. The positioning of the x-ray detector 20 should be stable, both within a scan and between scans, to within a fraction of a pixel, say, 0.1 mm (100 mm), for high-quality imaging without extra computation. A very stable bearing 30 is therefore desirable.

Apart from its mounting, the x-ray detector 20 may be a commercially available flat-panel x-ray detector, such as those supplied by Varian Medical Systems, Inc., of Salt Lake City, Utah.

Figure 4A:
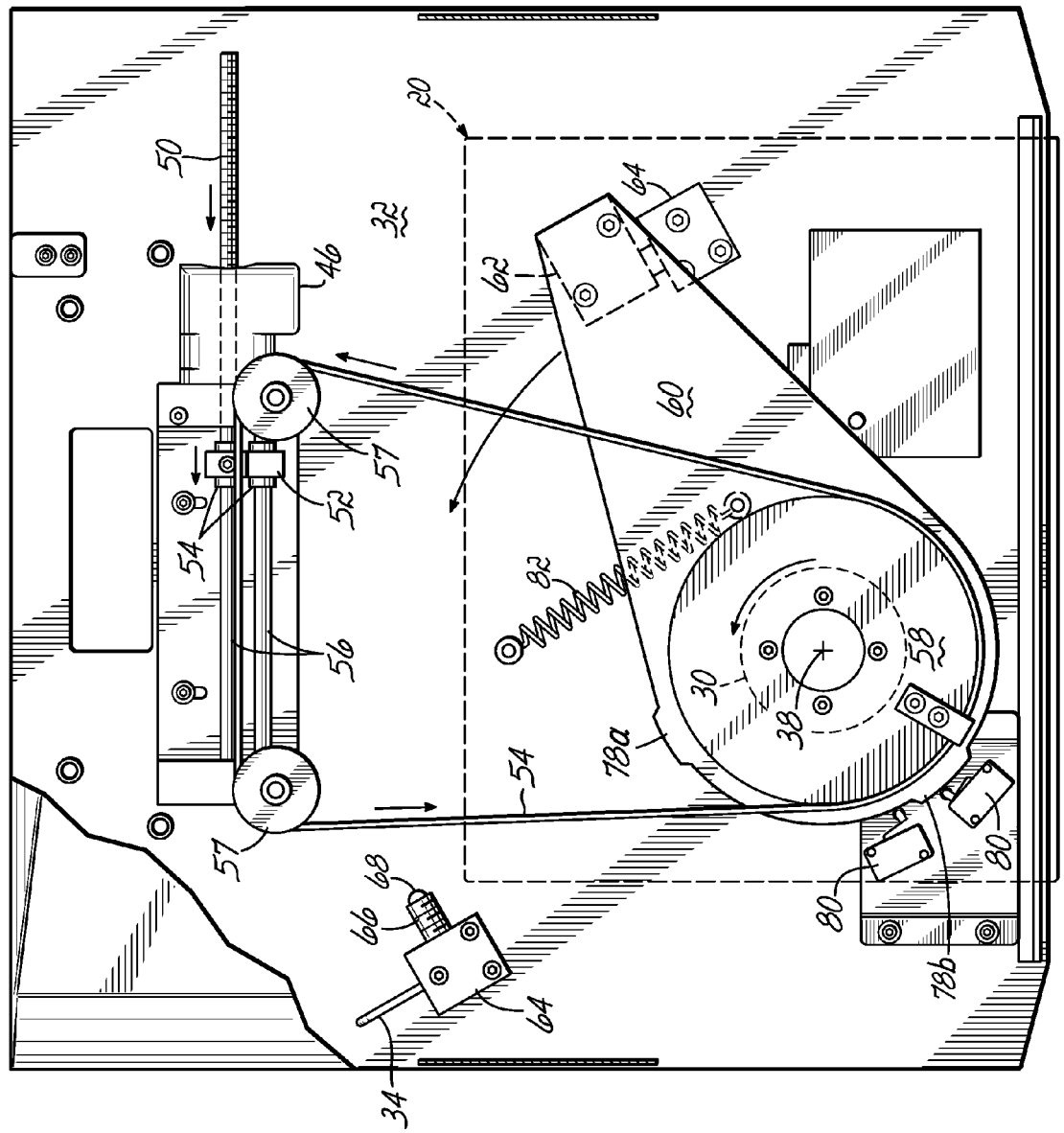
FIG. 4A is an elevational view of the outside of the detector end with the cover and a cable guard removed, in landscape orientation.
Figure 4B:
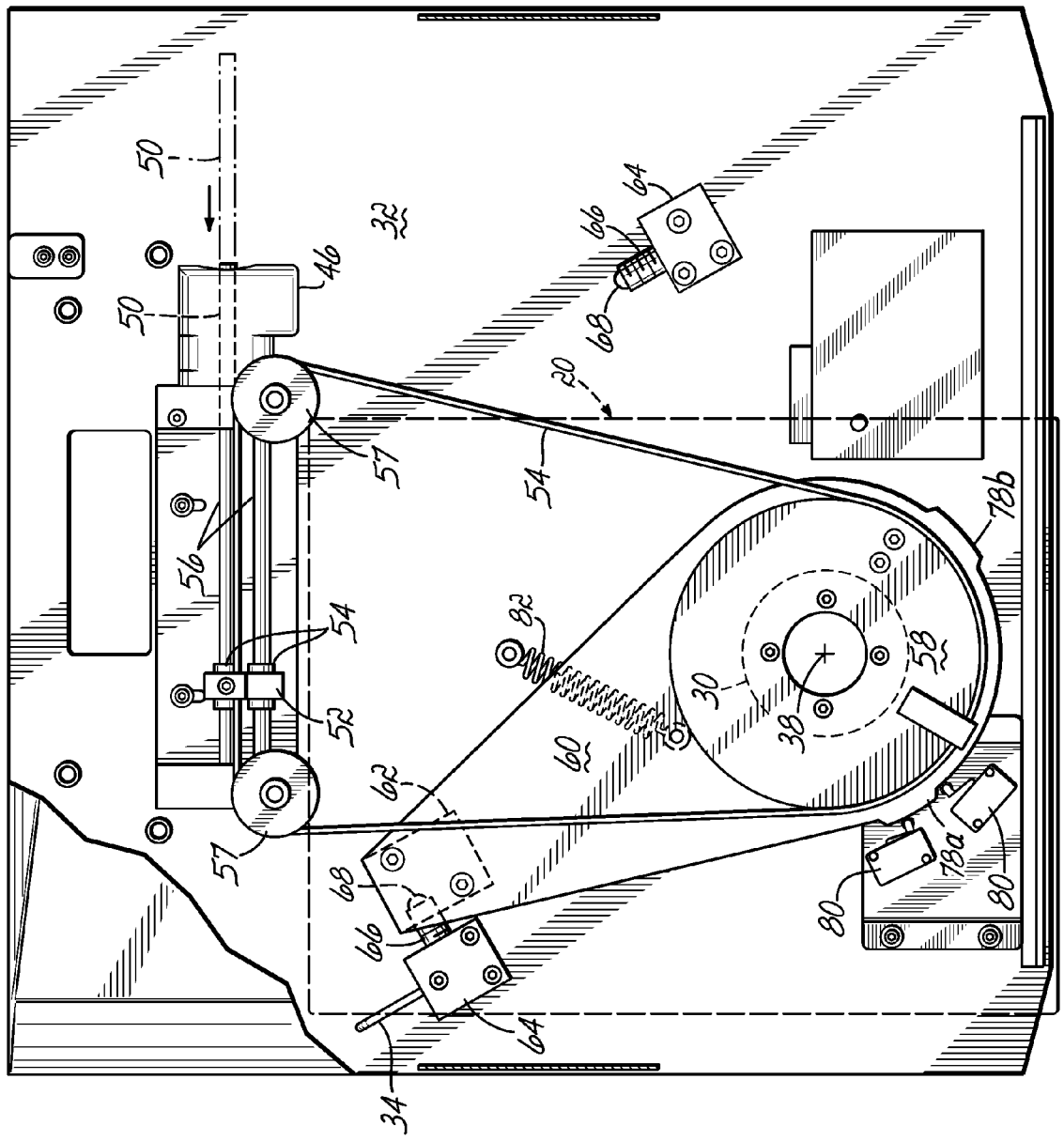
FIG. 4B is an elevational view of the outside of the detector end with the cover and a cable guard removed, in portrait orientation.

The position of the x-ray detector 20 is controlled by components visible in FIGS. 2, 4A, and 4B. A stepper motor 46 having an armature 48 (not shown) with internal threads extends and retracts an externally threaded shaft 50. The shaft is connected to a grab block 52 that has guides 54 that travel along two fixed rods 56 that resist the rotational forces of the motor. The grab block 52 is clamped to a belt 55. The belt passes over two pulleys 57, and around a journal 58 that is attached to the roller bearing 30. As the motor 46 extends and retracts the shaft 50, the belt moves clockwise and counter-clockwise to rotate the journal 58 and thereby the x-ray detector 20.

Figure 6:
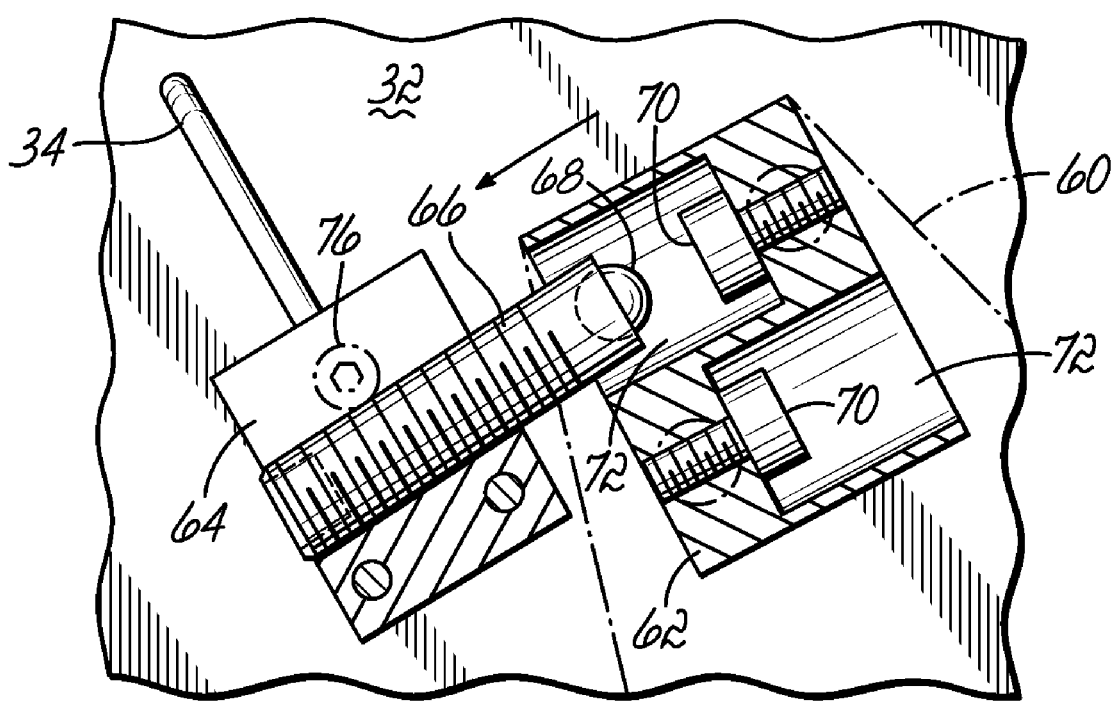
FIG. 6 is a detail view of a portion of the previous embodiments.

Attached to the journal 58 is an arm 60 carrying a head 62. As the journal 58 rotates, the head 62 describes an arc between two end stops 64 positioned so that the journal 58 and the arm 60 can rotate exactly ninety degrees between the end stops 64. The end stops 64 are provided with pins 66 for precise adjustment of the positions at which the head 62 is stopped by the end stops 64. The stops have hardened contact surfaces 68 and the head has hardened contact surfaces 70 (FIG. 6). The hardened surfaces are located within counter-bores 72 in the head so that both hardened surfaces are along a single plane extending from the detector axis 38. The non-contact end of the pins 66 rest against an adjustment screw 74 (not shown) within the end stop 64. The stop is split, so that tightening of a screw 76 clamps down on the pin 66.

To maintain precision it is important that the contacts do not wear or deform. A slow, low-power rotational speed prior to contact between the arms and the stops lessens impact. To this end, the journal 58 is provided with actuators 78a, 78b for a pair of limit switches 80 that detect when the journal 58 is near one of its end positions. The limit switches signal the position to the computer 13. At an appropriate time power to the motor is stopped, and gravity completes the movement of the arm and the detector. The grab block 52 comes to a stop when power to the motor is cut-off, but the arm and detector, driven by gravity, cause journal 58 to slip within the belt 54, until the contact 70 in the head 62 comes into contact with the contact 68. To further decrease the speed and force of rotation, a spring 82 is pivotally connected to the mounting panel 32 and the arm 60 to carry a portion of the weight.

The control of the position described above is just one way contemplated for low-speed contact. Alternatively, the movement of the journal 58 may be tracked in another way. For example, the actuators 78a, 78b and limit switches 80 may have secondary contacts arranged to signal to the computer 13 when the head 62 is a short distance from one of the end stops 64.

In operation, the pins 66 are set so that the end positions of the x-ray detector 20 are landscape and portrait positions with the rectangular array aligned with the gantry axis 36. The alignment may be precise to within a fraction of the size of a pixel over the length of the array, although the amount of precision required may be different for different embodiments of the invention. The computer 13 may be programmed to rotate the journal 58, and thus the x-ray detector 20, at a moderate speed, taking several seconds for a ninety degree rotation. Then, just before the head 62 reaches the end stop 64 at the far end of the rotation, the motor 46 is braked, and the head 62 closes gently against the pin 66, so that the x-ray detector 20 is accurately positioned without an impact that might damage any part of the system. In particular, it is desirable to avoid, as far as practical, deformation of the head 62 or the pins 66 that might result in the end position of the x-ray detector 20 drifting.

In use, the scanner 12 may be used with the x-ray detector 20 in landscape orientation for a computed tomography scan of the mouth region. A rectangular sensor array 22 that is 25 cm wide allows the detection of x-rays sufficiently far from the axis to allow for computed tomography of a quality sufficient for almost all dental and oral surgery. A rectangular sensor array 22 that is 20 cm high allows most human heads to be imaged over a region extending from just below the lower jaw to about the bottom of the eye-socket. If only a region of lesser height needs to be imaged for a specific purpose, the height of the x-ray beam can be reduced by an adjustable collimator to reduce the x-ray dose to the patient. A collimator with four independently controllable jaws is suitable, and in some jurisdictions is required, in order to collimate the x-ray beam to the changes in the position of the detector panel. Such collimators are well-known in the art and, in the interests of conciseness, are not further described here.

With the x-ray detector 20 in portrait orientation, a rectangular sensor array 22 that is 25 cm high allows most human heads to be imaged over a region extending from just below the lower jaw to about the level of the glabella, roughly eyebrow level. The extra height is required for certain types of orthodontic and orthognathic surgery, and a 25 cm high rectangular sensor array 22 is then sufficient for about 98% of human adults. The positioning of the detector axis 38 relative to the x-ray detector 20 results in the bottom of the rectangular sensor array 22 of the detector panel being at the same level in both portrait and landscape orientations, so that the positioning of the patient in the scanner 12 is identical in both portrait and landscape scanning, which reduces the risk that a scan has to be repeated because the patient was incorrectly positioned.

With a 20 cm by 25 cm rectangular sensor array 22 in portrait orientation, there is some loss of image quality, because of the reduced width of the detector. However, the positioning of the detector axis 38 relative to the x-ray detector 20 may be chosen so that one side of the rectangular sensor array 22 is the full 12.5 cm from the x-ray axis, with the other side of the array only 7.5 cm from the x-ray axis. The 12.5 cm extent on one side of the axis gives better coverage diametrally in computed tomography imaging than a panel extending to 10 cm on both sides of the x-ray axis, by using a known reconstruction method commonly referred to as "half beam mode." Although the image quality is less than with a 25 cm wide array, it has been found to be sufficient for most forms of orthodontic and orthognathic surgery. Where a high resolution image of the actual teeth is required, for example, for some forms of oral diagnosis or surgery, the 25 cm high full face scan can be combined with a second scan, using the x-ray detector 20 in 25 cm wide landscape orientation, but with the x-ray beam collimated to only 6 or 8 cm high. Such a double scan can be conducted with less x-ray dosage to the patient than would result from a full-face scan using two overlapping scans from a scanner with a fixed detector panel 25 cm wide by 20 cm high.

Certain commercially available detector panels suitable for use as the x-ray detector 20 are provided with built-in electronics for a high-resolution panoramic imaging mode, in which the x-ray beam is collimated to a narrow vertical slit, and only the detector pixels in the corresponding part of the detector array are read out. That mode greatly speeds the readout process, by reducing the number of pixels read. However, the available panels support that panoramic slit mode only in landscape orientation. High resolution full-face panoramic imaging is not usually needed, but the rotatable x-ray detector 20 of the present device allows switching between operating modes including a 25 cm high full-face scan and the panoramic slit mode where a fixed detector panel, in either orientation, could offer only one of those modes.

Various modifications and variations can be made in the present invention without departing from the spirit or scope of the invention. Thus, it is intended that the present invention cover modifications and variations of this invention provided they come within the scope of the appended claims and their equivalents.

As an example, a detector panel with an array of sensors 20 cm by 25 cm has been used. That is only an example, and detector panels of other sizes may be used.

As an example, a x-ray detector 20 positioned with the axis of the bearing 30 equidistant from two edges of the panel, so that the bottom edge and one side edge are at the same positions relative to the gantry in the landscape and portrait modes, has been described. Also described as an example is a x-ray detector 20 positioned with the axis of the bearing 30 equidistant from three edges of the panel, so that the bottom edge and one side edge are in the same positions relative to the gantry in the landscape and portrait modes. Certain reasons for those arrangements have been identified. However, other positions of the x-ray detector 20 relative to the axis of the bearing 30 are possible, and may be desirable for certain purposes or in certain scanner configurations.

FIG. 1 shows that the computer 13 on which the image data are processed and analyzed is connected to the scanner 12. A single computer 13 may both control the scanner 12 and process the data. Alternatively, part or all of the processing may be carried out on a separate computer. The data from the scanner 12 may be transferred from computer to computer in a convenient format, for example the DICOM format, at a convenient stage of the process. The data may, for example, be transferred directly from computer to computer or may, for example, be uploaded to and downloaded from a storage server. The detailed control of the motor 46 and the movement of the x-ray detector 20 may be controlled by a dedicated logic controller in the scanner 12, with the computer 13 or other external controller merely issuing a command to adopt a specified one of the portrait and landscape orientations, and receiving a signal confirming that the x-ray detector 20 is in a specific orientation.

What is claimed is:

1. An apparatus for dental and facial imaging, the apparatus comprising:
   a rotatable gantry having an axis of rotation generally in the direction of local gravitational vertical, the gantry configured to be rotated during an imaging procedure;
   a source of penetrating radiation mounted on the gantry;
   an elongated detector for detecting radiation from the source of penetrating radiation and producing image data, the detector mounted opposite the source on the gantry, and having a length, a long axis, and a short axis;
   the rotatable gantry, source, and detector configured to receive the head of a patient between the source and the detector when the patient is in an upright position, with the axis of rotation of the gantry passing through the patient's head;
   wherein the detector is mounted rotatably to the gantry and movable between a first position in which the long axis of the detector is generally perpendicular to the axis of rotation of the gantry and a second position in which the long axis of the detector is generally parallel to the axis of rotation of the gantry; and
   a computing device configured to receive image data from the detector and further configured to generate an image of at least a first portion of the patient's head if the detector is in the first position and to generate an image of at least a second portion of the patient's head if the detector is in the second position, wherein the second portion of the patient's head is different from the first portion of the patient's head.

2. Apparatus according to claim 1, wherein the detector is aligned so that the long axis is perpendicular to the axis of rotation of the gantry and the center of the detector is on the center axis of a beam of radiation from the source, which center axis intersects the axis of rotation of the gantry.

3. Apparatus according to claim 1, wherein the detector is mounted so that one corner is in the same position when the detector is in either of the first and second positions.

4. Apparatus according to claim 1, wherein the computing device is arranged to calculate at least one of voxel data and computed tomography pixel data.

5. Apparatus according to claim 1, wherein the detector is generally rectangular.

6. Apparatus according to claim 1 wherein the detector is mounted so that one edge is in the same horizontal plane in either of the first and second positions.

7. Apparatus according to claim 1 wherein the detector is mounted so that the lower edge perpendicular to the axis of gantry rotation is in the same horizontal plane in either of the first and second positions.

8. Apparatus according to claim 1 wherein the detector is a flat-panel detector.

9. Apparatus according to claim 1 wherein at least one of the images of the first and second portions of the patient's head is a CT image.

10. Apparatus according to claim 1 wherein at least one of the images of the first and second portions of the patient's head is a panoramic image.

11. Apparatus according to claim 1 wherein the source of penetrating radiation has an x-ray axis, and wherein a center of the second position is offset from the x-ray axis.

12. Apparatus according to claim 11 wherein the detector is movable between the first and second positions by rotation of the detector around a detector axis which is offset from a center of the detector.

13. A method for dental and facial imaging using an apparatus comprising a computing device, a rotatable gantry having an axis of rotation generally in the direction of local gravitational vertical, a penetrating radiation source mounted on the gantry, and an elongated detector mounted opposite the source on the gantry and having a length, a long axis, and a short axis, the method comprising:
   rotating the detector between a first position in which the long axis of the detector is generally perpendicular to the axis of rotation of the gantry and a second position in which the long axis of the detector is generally parallel to the axis of rotation of the gantry;
   generating an image of at least a first portion of a patient's head if the detector is in the first position; and
   generating an image of at least a second portion of the patient's head if the detector is in the second position, wherein the second portion of the patient's head is different from the first portion of the patient's head, and wherein each of the steps of generating an image of at least a first portion and second portion comprises:
      receiving the patient's head between the source and the detector when the patient is in an upright position, with the axis of rotation of the gantry passing through the patient's head, rotating the gantry about the axis of rotation of the gantry, generating penetrating radiation by the radiation source during the step of rotating the gantry, detecting the penetrating radiation by the elongated detector to produce image data, and receiving the image data by the computing device.

14. The method according to claim 13, further comprising aligning the detector so that the long axis is perpendicular to the axis of rotation of the gantry and the center of the detector is on the center axis of a beam of radiation from the source, which center axis intersects the axis of rotation of the gantry.

15. The method according to claim 13, further comprising positioning the detector so that one corner is in the same position when the detector is in either of the first and second positions.

16. The method according to claim 13, further comprising calculating, by the computing device, at least one of voxel data and computed tomography pixel data.

17. The method according to claim 13, wherein the step of detecting the penetrating radiation comprises using a generally rectangular detector to detect the penetrating radiation.

18. The method according to claim 13 further comprising positioning the detector so that one edge is in the same horizontal plane in either of the first and second positions.

19. The method according to claim 13 further comprising positioning the detector so that the lower edge perpendicular to the axis of gantry rotation is in the same horizontal plane in either of the first and second positions.

20. The method according to claim 13 wherein the step of detecting the penetrating radiation comprises using a flat-panel detector.

21. The method according to claim 13 wherein at least one of the images of the first and second portions of the patient's head is a CT image.

22. The method according to claim 13 wherein at least one of the images of the first and second portions of the patient's head is a panoramic image.

23. The method according to claim 13 wherein the source of penetrating radiation has an x-ray axis, and wherein a center of the second position is offset from the x-ray axis.

24. The method according to claim 23 wherein the step of rotating the detector between the first and second positions comprises rotating the detector around a detector axis which is offset from a center of the detector.

* * * * *